United States Patent [19]

Helfgott et al.

[11] 4,314,560
[45] Feb. 9, 1982

[54] POWERED HANDPIECE FOR ENDOPHTHALMIC SURGERY

[76] Inventors: Maxwell A. Helfgott, 5640 Bradley Blvd., Bethesda, Md. 20014; Gerald N. Helfgott, 5513 Uppingham St., Chevy Chase, Md. 20015

[21] Appl. No.: 97,984

[22] Filed: Nov. 28, 1979

[51] Int. Cl.$^3$ .............................................. A61B 17/32
[52] U.S. Cl. .................................. 128/305; 128/276
[58] Field of Search .................... 128/305, 276, 24 A, 128/751, 752, 755; 30/241

[56] References Cited

U.S. PATENT DOCUMENTS

| | | | |
|---|---|---|---|
| 3,528,425 | 9/1970 | Banko | 128/305 |
| 3,589,363 | 6/1971 | Banko et al. | 128/276 |
| 3,659,607 | 5/1972 | Banko | 128/305 |
| 3,732,858 | 5/1973 | Banko | 128/305 X |
| 3,734,099 | 5/1973 | Bender et al. | 128/305 |
| 3,736,938 | 6/1973 | Evvard et al. | 128/305 |
| 3,776,238 | 12/1973 | Peyman et al. | 128/305 |
| 3,805,787 | 4/1974 | Banko | 128/276 |
| 3,809,093 | 5/1974 | Abraham | 128/305 |
| 3,812,855 | 5/1974 | Banko | 128/276 |
| 3,815,604 | 6/1974 | O'Malley et al. | 128/305 |
| 3,844,272 | 10/1974 | Banko | 128/305 X |
| 3,857,387 | 12/1974 | Shock | 128/305 X |
| 3,882,872 | 5/1975 | Douvas et al. | 128/305 |
| 3,884,237 | 5/1975 | O'Malley et al. | 128/303.14 |
| 3,884,238 | 5/1975 | O'Malley | 128/305 |
| 3,902,495 | 9/1975 | Weiss et al. | 128/276 |
| 3,906,954 | 9/1975 | Baehr et al. | 128/305 |
| 3,920,014 | 11/1975 | Banko | 128/230 |
| 3,937,222 | 2/1976 | Banko | 128/305 |
| 3,945,375 | 3/1976 | Banko | 128/6 |
| 3,976,077 | 8/1976 | Kerfoot | 128/305 |
| 3,990,453 | 11/1976 | Douvas et al. | 128/305 |
| 3,994,297 | 11/1976 | Kopf | 128/276 |
| 3,996,935 | 12/1976 | Banko | 128/276 |
| 4,007,742 | 2/1977 | Banko | 128/230 |
| 4,011,869 | 3/1977 | Seiler | 128/276 |
| 4,019,514 | 4/1977 | Banko | 128/230 |
| 4,063,557 | 12/1977 | Wuchinich et al. | 128/276 |
| 4,099,529 | 7/1978 | Peyman | 128/305 |
| 4,108,182 | 8/1978 | Hartman et al. | 128/305 |
| 4,117,843 | 10/1978 | Banko | 128/230 |

FOREIGN PATENT DOCUMENTS

| | | | |
|---|---|---|---|
| 600781 | 7/1934 | Fed. Rep. of Germany | 128/305 |
| 2362157 | 11/1974 | Fed. Rep. of Germany | 128/305 |
| 2456755 | 8/1976 | Fed. Rep. of Germany | 128/305 |
| 2758909 | 9/1978 | Fed. Rep. of Germany | 128/305 |
| 428749 | 10/1974 | U.S.S.R. | 128/305 |

OTHER PUBLICATIONS

Kreiger et al., "A Vitrectomy Instrument in Stereotoxic Intraocular Surgery", *Am. J. Ophthal.* 76:527 (Oct. 1973).

Scheie, "Aspiration of Congenital or Soft Cataracts: A New Technique", *Am. J. Ophthal*, 50:1048 (1960).

Machemer et al., "Vitrectomy: Apars Plana Approach", *Trans Am. Acad Opthal. Otolaryng*, 75:813 (1971).

Peyman et al., "Experimental Vitrectomy: Instrumentation and Surgical Technqiue", *Arch. Ophthal*, 86:548 (1971).

Douvas, "The Cataract Roto-Extractor (A Preliminary Report)", *Trans. Am. Acad. Ophthal. Otolaryng*, 77:792 (1973).

*Primary Examiner*—Michael H. Thaler
*Attorney, Agent, or Firm*—Irons and Sears

[57] ABSTRACT

A powered handpiece for use in endophthalmic surgery comprises a projecting tubular surgical instrument including an inner tubular member slidably received within a coaxial outer tubular member for reciprocation therein, a pneumatic actuator for imparting reciprocation to the inner tubular member, and a coupling member interposed between the actuator and the surgical instrument for transmitting reciprocating motion from the actuator to the inner tubular member. The coupling member has a recessed configuration permitting a flexible suction or infusion tube to be connected to the proximal end of the inner tubular member. The pneumatic actuator, coupling member, and proximal portion of the tubular surgical instrument are received in tandem arrangement by a housing having a side opening for the flexible suction or infusion tube and a separable anterior section for permitting interchangeability among different surgical instruments.

5 Claims, 8 Drawing Figures

POWERED HANDPIECE FOR ENDOPHTHALMIC SURGERY

BACKGROUND OF THE INVENTION

1. Field of the Invention

The present invention relates to powered handpieces for use in endophthalmic surgery.

2. Description of the Prior Art

Endophthalmic surgery, or surgery on an intact and normally pressurized eye, represents an important and relatively recent development in the field of ophthalmology. In this technique, the existing optical pathways of the pressurized ocular globe are utilized for visualization during delicate intraocular manipulations. Maintenance of positive intraocular pressure, moreover, tends to preserve and stabilize the spatial relationships among the various intraocular tissues.

The archetypal endophthalmic procedure is the cataract aspiration technique of extracapsular cataract surgery described by Scheie, *Am. J. Ophthal.* 50:1048 (1960), wherein an instrument is passed through a small incision at the margin of the cornea into the anterior aqueous chamber of the eye to incise the anterior capsular membrane of the lens. The aqueous, which leaks out during this manipulation, is replaced by a gravity-fed infusion of physiologic saline through a cannula inserted into the anterior chamber through a second small incision. A blunt needle is then inserted through the first incision into the lens, whereupon gentle suction aspirates the soft lens substance leaving the posterior capuslar membrane in place. Whatever volume is removed or leaks from the two small incisions is replaced by the continuous gravity feed of saline. Absent any seepage or applied suction, the pressure in the eye stabilizes at a point determined by the physical elevation of the saline column above the level of the eye. At the end of the procedure, all tubes are withdrawn and the incisions are sutured.

Conceptually, all modern endophthalmic procedures are variations and refinements of the foregoing technique. In vitrectomy, for example, an incision is made through the scleral coat of the eye between the iris and the anteromost retina. A tract is cut with a long, sharp knife into the vitreous, and the tip of the vitrectomy instrument is placed in the eye. Infusion is provided through a separate incision or through cannula concentric with the vitrectomy instrument itself. Gentle aspiration provided through the tip of the vitrectomy instrument engages vitreous or other intraocular tissues, which are then sheared or sliced in small bits and removed from the eye through an aspiration tube. Illumination is provided by optical fibers which may be concentric with the vitrectomy instrument or inserted separately. The procedure is visualized with a high magnification operating microscope. Actuation of the various functions at the instrument tip is usually by remote foot control.

The earliest powered vitrectomy instruments utilized rotary cutting elements. See, e.g., Machemer et al., *Trans. Am. Acad. Ophthal. Otolaryng.* 75:813 (1971). Rotary instruments, however, tended to introduce undesirable pulling or shearing to the tissue being severed. Efforts to avoid these effects led to the development of linearly reciprocating cutting instruments, an early sample of which is described by Peyman and Dodich, *Arch. Ophthal.* 86:548 (1971). The instrument portion of the handpiece consists of two concentric tubes with a hole near the distal end of the outer tube. Cutting is performed by the chopping action of the sharpened end of the inner tube against the plane interior end of the outer tube. Suction applied to the inner tube urges the tissue to be severed into the hole in the outer tube and then removes the severed bits of tissue from the eye. Infusion is provided through a small tube running parallel to the outer concentric tube. The necessary powered reciprocation of the inner tube relative to the fixed outer tube is provided by a small electrical solenoid, the oscillation rate of which can be varied. A description of this handpiece can also be found in U.S. Pat. No. 3,776,238, to Peyman et al.

Although electrical solenoid devices provide a readily adjustable source of linear reciprocating motion, they also possess numerous drawbacks which limit their utility in a surgical environment. They tend to be relatively heavy, for example, which renders the handpiece somewhat inconvenient to manipulate. During sustained operation, solenoid devices also tend to generate significant amounts of heat which must be isolated from delicate tissues. Moreover, since the solenoid is an integral part of the handpiece and must be supplied with an electrical current, a potential electrical hazard is presented.

Pneumatic power sources possess none of the foregoing disadvantages. Pneumatic devices are readily adaptable to linear reciprocating operation, do not inherently generate heat, and can be constructed from lightweight materials. To the extent that electrical controls are necessary, they can be confined to a pneumatic power supply unit that is connected to the handpiece by a nonconducting pneumatic supply line and is thus well isolated from the surgical site. Pneumatic devices, moreover, tend to produce a more evenly modulated power pulse than is obtainable from electrical solenoid devices. These factors render pneumatic devices well suited as power sources for powered vitrectomy instruments, and a number of pneumatically operated handpieces have been developed for ophthalmic use.

With the continual refinement of endophthalmic surgical techniques and the proliferation of specialized reciprocating instruments based on the previously-described prototype of Peyman and Dodich, there has arisen a need for a pneumatic handpiece which is compact for convenient manipulation during delicate surgical procedures, simple in construction, safe to operate in a surgical environment, and versatile in the sense of accommodating a number of different endophthalmic instruments in an interchangeable manner. Prior art pneumatic handpieces invariably fall short in one or more of these respects.

One known type of pneumatic handpiece is described in U.S. Pat. Nos. 3,815,604 and 3,884,237, both to O'Malley et al. The disclosed handpiece consists generally of a cylindrical housing, an end cap for receiving one end of a projecting sharp-edged stainless steel tube, and a piston which is slidably received within the housing for providing reciprocating motion to a second stainless steel tube coaxially arranged within the first. Near its distal end, the inner tube has one or more holes into which vitreous tissue is drawn by suction and severed as the distal end of the inner tube is moved inward past the sharpened edge of the outer concentric tube, thereby implementing a pull-type cutting operation. Alternatively, the inner tube is sharpened at its distal end and the outer tube is provided with a sharpened distal opening to form a push-type cutter. In both embodiments, the inner tube is affixed directly to the piston and extends axially through to the opposite side thereof for connection to a flexible evacuation line which then passes out the back of the handpiece. The alternate air and suction pulses required for reciprocating the piston are supplied through a larger-diameter tube which coaxially receives the smaller evacuation line and also connects to the back of the handpiece. Although this manner of construction makes possible a fairly simple handpiece, interchangeability is sacrificed since the inner tube of the coaxial cutting assembly is affixed directly to the piston that reciprocates it. In addition, a potential problem of safety is presented by locating the connection point between the evacuation line and the inner tube within the compression zone behind the piston. If this connection were to fail for some reason, a direct path would be established between the pneumatic power supply and the interior of the eye by way of the inner tube, with possibly catastrophic results.

A similar pneumatic handpiece is disclosed in U.S. Pat. No. 3,884,238, also to O'Malley et al. As in the case of the previously-described handpiece, the inner reciprocating tube of the coaxial cutting assembly is affixed directly to the pneumatic piston and passes axially through a bore in the piston for connection to an evacuation tube on the opposite side thereof. In this case, however, the evacuation tube is a rigid metallic structure which slides through a bearing member at the back of the handpiece as the piston reciprocates. In addition, a metallic bellows is provided within the handpiece for containing the pneumatic compression and suction pulses required for reciprocating the piston. Isolation of the pneumatic power pulses from the inner tube of the cutting assembly still depends, however, on the integrity of the connection between the proximal end of the inner tube and the rigid evacuation tube on the pressurized side of the piston. Interchangeability of the coaxial tubular cutting assembly is again impeded, moreover, by the integral mechanical connection between the inner tube and the components of the reciprocating piston assembly.

A further known type of pneumatic handpiece for ophthalmic applications is described in U.S. Pat. No. 3,994,297, to Kopf. In this device, reciprocating motion for a coaxial tubular cutting assembly is provided by a piston which is displaced alternately in one direction by pulses of compressed air from a pneumatic source and in the other direction by a compressed return spring contained within the handpiece. The inner tube of the cutting assembly is rigidly connected to the forward portion of the piston and communicates with an axial bore formed therein. The axial bore communicates with an annular port, also formed in the forward section of the piston, which in turn slidably communicates with a vacuum passageway extending longitudinally along the inner periphery of the molded case of the handpiece and coupled to a vacuum line at the back of the handpiece. A pair of O-rings are provided to seal off the sliding connection between the annular port in the forward part of the piston and the vacuum passageway in the molded case of the handpiece from the remaining passageways and cavities of the handpiece. While this arrangement has the advantage of effectively isolating the vacuum connection to the inner tube of the cutting assembly from the pressurized zone behind the pneumatic piston, this is done at the expense of simplicity of construction, given the need for a rather elaborately bored and ported piston and the seals required for maintaining the sliding vacuum connection. In addition, the provision of a longitudinal vacuum passageway running parallel to the centrally located piston assembly necessitates an undesirable increase in the overall diameter of the handpiece. Finally, the rigid mechanical connection of the inner tube of the tubular cutting assembly to the reciprocating piston of the handpiece renders interchangeability of the cutting assembly impractical, if not impossible.

SUMMARY OF THE INVENTION

A powered handpiece for endophthalmic surgery in accordance with the present invention comprises, in general, a projecting tubular surgical instrument including coaxial inner and outer tubular members, the inner tubular member being slidably received within the outer tubular member for linear reciprocation therein, a pneumatic or other type of linear actuator for producing linear reciprocating motion from a suitable power source, a coupling member interposed between the linear actuator and the projecting tubular surgical instrument for transmitting linear reciprocating motion from the linear actuator to the inner tubular member, and a housing for receiving in tandem arrangement the linear actuator, the coupling member, and the proximal portion of the projecting tubular surgical instrument. The coupling member has a configuration permitting a flexible tube to be connected to the proximal end of the inner tubular member for carrying out suction or infusion through the inner tubular member during reciprocation thereof. When the linear actuator is of the preferred pneumatic type, the coupling member provides complete fluidic isolation between the actuator and the suction or infusion connection to the inner tubular member while preserving the mechanical linkage necessary to transmit linear reciprocating motion from the actuator to the inner tubular member.

In a preferred embodiment of the invention, a return spring is provided in operative association with the inner tubular member for acting in opposition to the motion produced by the linear actuator as transmitted to the inner tubular member by the coupling member. Reciprocation may therefore be imparted to the inner tubular member without the necessity for any rigid mechanical connection, other than a physically abutting relationship, between the coupling member and either the inner tubular member or the linear actuator. Convenient interchangeability of surgical instruments is then realized by providing a separable anterior section of the housing for receiving the return spring and the proximal portion of the projecting tubular surgical instrument, the remaining components of the handpiece being received in a posterior section of the handpiece.

The inner tubular member of the projecting tubular surgical instrument preferably includes a rigidly attached platform member spaced from its proximal end by a distance sufficient to permit the attachment of a flexible suction or infusion tube to the proximal end of the inner tubular member. One end of the coupling member is contoured for abutting the platform member in order to transmit linear reciprocating motion to the inner tubular member via the platform member while also providing clearance for the connection of the flexible suction or infusion tube to the proximal end of the inner tubular member. The return spring may then comprise a coil spring encircling a portion of the inner tubular member and compressed between the platform member and an interior surface of the separable anterior section of the housing.

In a particularly preferred embodiment of the invention, the anterior and posterior housing sections are generally cylindrical, so as to form a smooth cylindrical housing when coupled together, and the platform member is generally cylindrical and coaxial with the inner tubular member to which it is affixed. The coupling member includes a substantially semicylindrical portion having a substantially semicylindrical cavity therein which extends to and opens onto the end of the coupling member that abuts the platform member. The cavity provides the necessary clearance for the connection of the flexible suction or infusion tube to the proximal end of the inner tubular member of the projecting surgical instrument, and has dimensions sufficient to receive a lengthwise portion of a flexible tube which has been thus connected. The coupling member further includes a closed end portion opposite the end of the coupling member which abuts the platform member, and adjoining the substantially semicylindrical portion of the coupling member, for abutting the linear actuator in order to receive linear reciprocating motion therefrom. The closed end portion includes an inclined guide surface adjacent to the semicylindrical cavity for causing the flexible tube to bend smoothly to form an angle with respect to the longitudinal axis of the inner tubular member. The posterior section of the housing has an opening in the cylindrical side surface thereof at a point adjacent the coupling member for allowing the flexible tube to pass loosely out of the housing at this angle. Preferably, at least a portion of the wall of this opening is inclined similarly to the inclined guide surface of the coupling member, so that the inclined guide surface and the similarly inclined wall portion of the opening cooperate to cause the flexible tube to bend smoothly at the aforesaid angle.

When the linear actuator is of the pneumatic type, as in the preferred embodiment, this manner of construction avoids many of the problems and limitations associated with the pneumatic handpieces heretofore available. As noted previously, the coupling member of the present handpiece provides complete fluidic isolation between the pneumatic actuator and the suction or infusion connection to the inner tubular member of the projecting tubular surgical instrument while preserving the mechanical linkage necessary for the transmission of linear reciprocating motion from the pneumatic actuator to the inner tubular member. Moreover, as a consequence of directing the flexible suction or infusion tube out the side of the handpiece at a point adjacent the coupling member, a simple and compact in-line arrangement of the handpiece components is possible and the need for elaborate fluid channels and sealing techniques which render presently available handpieces unnecessarily large and complex is avoided.

At the same time, the structural arrangement of the preferred embodiment of the present handpiece allows for convenient interchangeability among different specialized intraocular surgical instruments. When the anterior section of the housing is detached and the flexible suction or infusion tube disconnected from the proximal end of the inner tubular member, the detached anterior housing section carries with it only the surgical instrument itself, the attached platform member, and the return spring, which together comprise a relatively minor portion of the assembled handpiece. Since there is no necessity for a rigid mechanical connection between the platform member and the abutting coupling member, the substitution of a new surgical instrument merely requires the reconnection of the flexible suction or infusion tube and the attachment of the new anterior housing section to the main body of the handpiece.

Although the powered handpiece of the present invention will accommodate a number of different specialized intraocular surgical instruments, a preferred instrument comprises an outer tubular member having an aperture near its distal end and an inner coaxial tubular member slidably received within the outer tubular member for linear reciprocation therein, and having a sharpened edge at or near its distal end. As is well known in the art, instruments of this general type are used for severing and removing unwanted vitreous or other intraocular tissue by applying a source of suction to the inner tubular member and inducing rapid linear reciprocation of the inner tubular member within the outer tubular member. The vitreous tissue to be removed is drawn by the applied suction into the aperture in the outer tubular member and severed in small bits by the passing sharp edge of the inner tubular member. The severed bits of tissue are then evacuated through the inner tubular member and into a suitable external receptacle by virtue of the applied suction. Depending upon their configurations, vitrectomy instruments of this general type may or may not require a fixed rotational orientation of the inner tubular member with respect to the outer coaxial tubular member. When required, such a fixed rotational orientation is readily provided for in the handpiece of the present invention by means of a key-and-groove mating arrangement between the platform member and the interior surface of the separable anterior housing section in which the particular surgical instrument is received. Accordingly, it is not necessary to maintain a fixed rotational orientation between the remaining components in the main body of the handpiece.

BRIEF DESCRIPTION OF THE DRAWINGS

The advantages and novel features of the present invention will be more readily apprehended from the following detailed description in connection with the appended drawings, in which.

Throughout the drawings, like reference numerals identify like parts.

DETAILED DESCRIPTION OF THE PREFERRED EMBODIMENT

Figure 1:
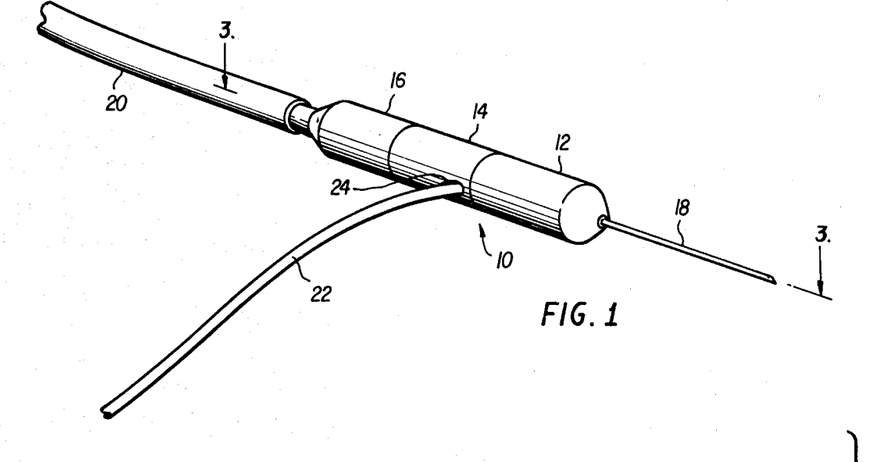
FIG. 1 is a perspective view of an assembled pneumatic handpiece in accordance with the present invention.

FIG. 1 is a perspective view of an assembled pneumatic handpiece 10 in accordance with the present invention. The handpiece includes a cylindrical housing comprising an anterior cylindrical section 12, a central cylindrical section 14, and a rear cylindrical section 16. For reasons which will shortly become apparent, the central section 14 and rear section 16 of the housing may be thought of as one and will occasionally be collectively referred to hereinafter as the posterior section of the handpiece or, in connection with the components they receive, as the main body of the handpiece.

The anterior section 12 of the housing receives the proximal portion of a projecting tubular surgical instrument which includes an outer tubular member 18 and an inner tubular member 48 (illustrated in FIG. 2) which is coaxially and slidably received within the outer tubular member 18 for linear reciprocation therein. Flexible pneumatic supply line 20 attaches to the rear section 16 of the handpiece by means of a Luer fitting or the like and is connected at its opposite end to a suitable pneumatic power supply, not shown, for providing the intermittent pulses of compressed air or other gas that are used to impart reciprocating motion to the inner tubular member of the surgical instrument by means of a pneumatic linear actuating device. Flexible tube 22 is connected at a point within the housing of the handpiece to the proximal end of the inner tubular member 48, and passes loosely out of the handpiece through an opening 24 formed in the cylindrical side surface of the housing. Depending on the type of projecting tubular endophthalmic instrument which is carried by the anterior section 12 of the housing, flexible tube 22 may be used for suction (i.e., evacuation) or infusion.

Figure 2:
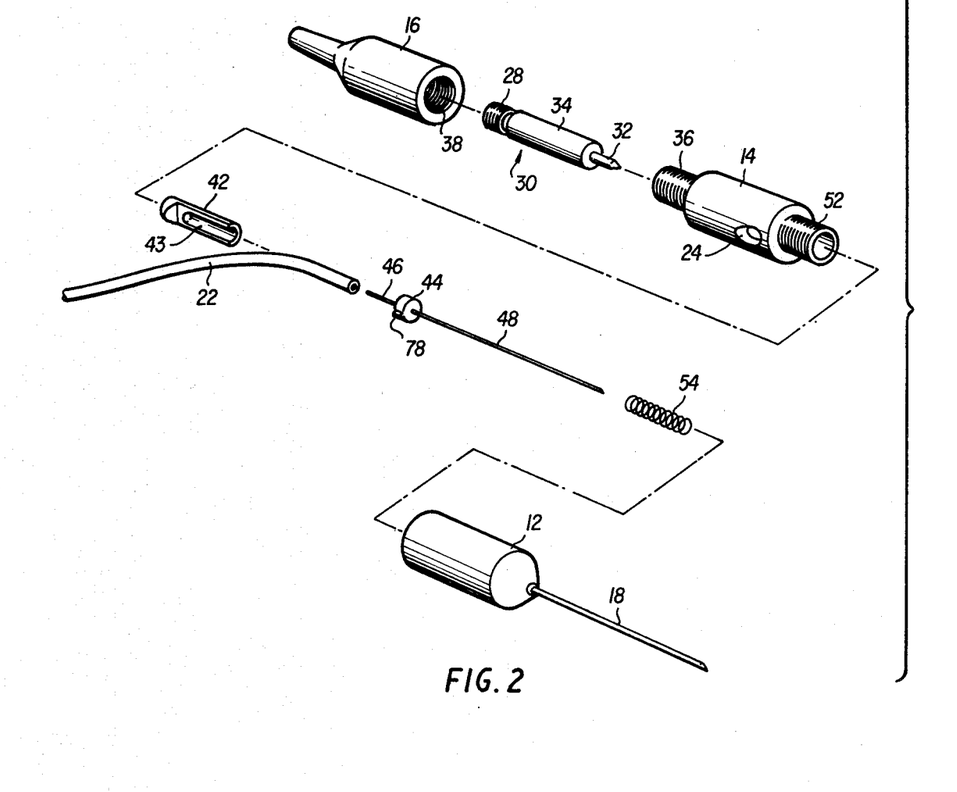
FIG. 2 is an exploded view of the handpiece of FIG. 1, illustrating the various components thereof.
Figures 3, 4, 5A, 5B, 6A, 6B:
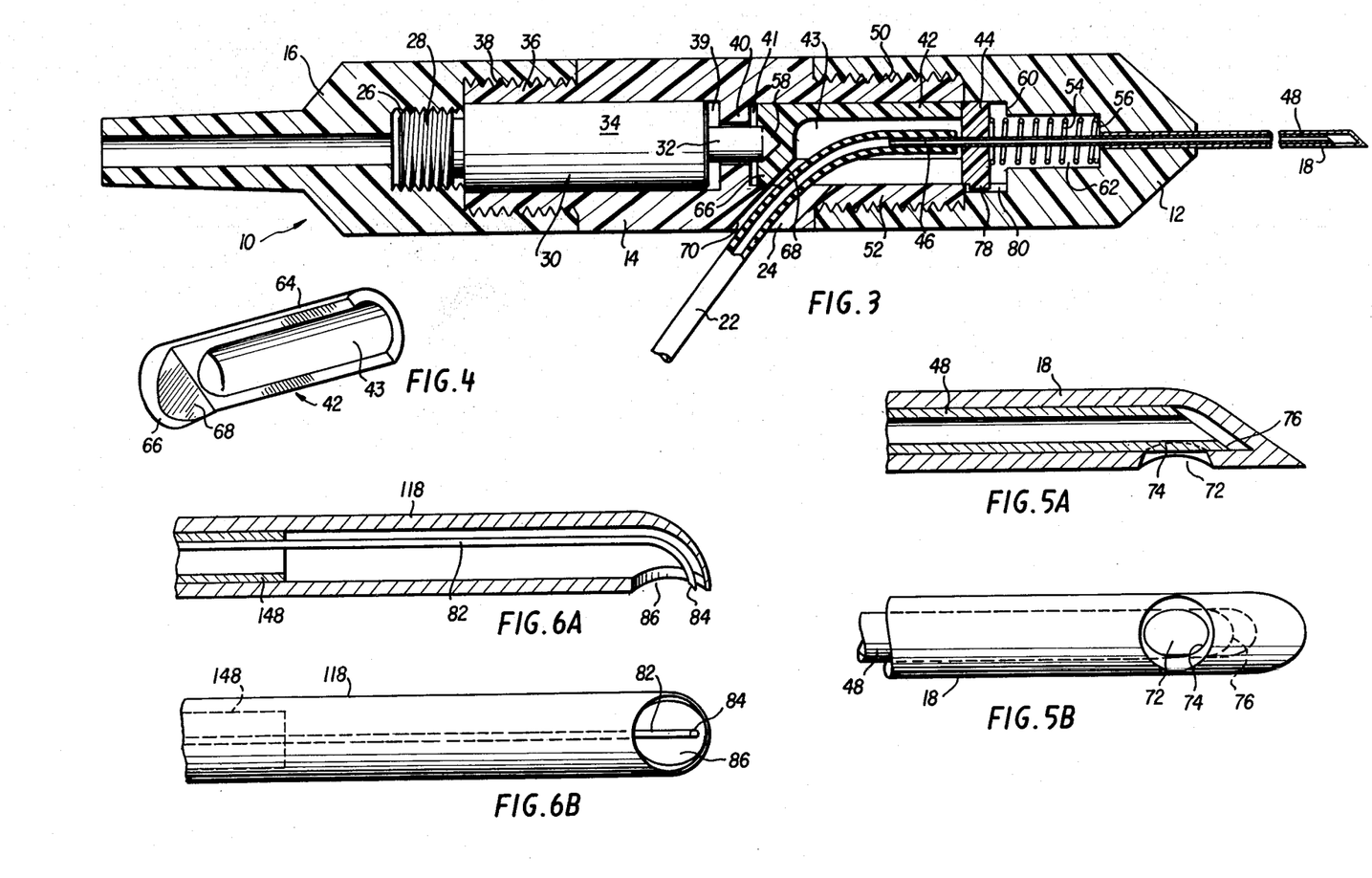
FIG. 3 is a side sectional view of the handpiece taken along the line 3—3 of FIG. 1, with the pneumatic supply line and part of the projecting tubular surgical instrument omitted.
FIG. 4 is a perspective view of the coupling member seen in FIGS. 2 and 3.
FIGS. 5A and 5B are enlarged side sectional and plan views, respectively, of the distal portion of an endophthalmic vitrectomy instrument useful in connection with the handpiece of the present invention.
FIGS. 6A and 6B are enlarged side sectional and plan views, respectively, of the distal portion of an alternative endophthalmic instrument which may be accommodated by the handpiece of the present invention.

The various individual components of the present handpiece and their relative orientation will now be described with reference to FIGS. 2 and 3. FIG. 2 is an unassembled or exploded view of the handpiece of FIG. 1 with the pneumatic supply line 20 omitted for simplicity. FIG. 3 is a side sectional view of the handpiece taken along the line 3—3 of FIG. 1, with the pneumatic supply line again removed and the median portion of the projecting tubular surgical instrument omitted.

Referring generally to FIG. 2, the handpiece will be seen to include rear housing section 16, a pneumatic actuator 30, central housing section 14, coupling member 42, inner tubular member 48 to which platform member 44 is rigidly attached, return spring 54, and anterior housing section 12 in which the proximal end of outer tubular member 18 is received and supported. Flexible suction or infusion tube 22 is provided for connection to the proximal end 46 of the inner tubular member 48 and passes out the side of the handpiece through the opening 24 in the central housing section 14 as shown in FIG. 1.

As indicated in FIG. 3, rear section 16 of the housing is provided with internal threads 26 for making airtight engagement with the rear threaded fitting 28 of the pneumatic actuator 30. Pneumatic actuator 30 contains an internal piston and spring return for urging the pusher member 32 linearly outward with respect to the cylindrical body portion 34 of the actuator in response to intermittent pneumatic pressure pulses supplied through the fitting 28. In the applicants' prototype, the pneumatic actuator 30 was a Model SM-2 micropneumatic device manufactured by Clippard Instrument Laboratory of Cincinnati, Ohio. A suitable pneumatic power supply for providing intermittent positive pressure pulses to operate the pneumatic actuator is the Model V-3002 console manufactured by David Kopf Systems of Tujunga, California. Pneumatic power supplies producing alternating positive and negative pressure pulses can also be used, but negative pressure pulses are not necessary when, as here, the pneumatic actuator includes an internal spring return.

It should be understood that the pneumatic actuator 30 may be operated by other compressed fluids in addition to compressed air. Further, as will be more fully appreciated hereinafter, the present handpiece possesses a number of advantages, particularly its ability to accommodate different surgical instruments in an interchangeable manner, that are preserved even if the actuator is, for example, an electrical solenoid rather than a pneumatic device. Pneumatic devices are preferred, however, for reasons of electrical isolation, light weight, low operating temperature and smoothness of operation. Moreover, the structural arrangement of the present handpiece will be seen to provide an inherent fluidic isolation for the flexible suction or infusion tube connection that renders it particularly advantageous for use with a pneumatic power source. For purposes of describing the preferred embodiment of the present handpiece, therefore, the linear actuator 30 will hereinafter be assumed to be pneumatic.

Central section 14 of the cylindrical housing of the handpiece includes an externally threaded portion 36 for engaging a correspondingly internally threaded portion 38 of the rear housing section 16. When threadably engaged, the rear section 16 and central section 14 of the housing together define an internal cylindrical cavity 39 for receiving the pneumatic actuator 30. An annular wall 40 located a short distance behind the opening 24 in the central housing section 14 defines the forward extent of the cavity 39. Pusher member 32 of the pneumatic actuator protrudes through the circular aperture defined by the annular wall 40 in order to make abutting contact with the coupling member 42 as will be described hereinafter. Normally, once the pneumatic actuator 30 is in place there is no reason to separate the rear section 16 of the housing from the central section 14. During initial assembly of the handpiece, therefore, the housing sections 14 and 16 may be permanently bonded together by a suitable adhesive or the like and will then together comprise the posterior section of the housing.

On the opposite side of the annular wall 40 in the central housing section 14 there is defined a further cylindrical cavity 41 for slidably receiving the coupling member 42. As will be described in more detail hereinafter, coupling member 42 provides an abutting mechanical connection between the reciprocating pusher member 32 of the pneumatic actuator 30 and the cylindrical platform member 44 press-fitted onto the inner tubular member 48 at a point near its proximal end 46. At the same time, the recessed configuration of the coupling member 42 resulting from the open semicylindrical cavity 43 formed therein permits flexible tube 22 to be connected to the proximal end 46 of the inner tubular member 48 for carrying out suction or infusion through the inner tubular member during reciprocation thereof within the outer coaxial tubular member 18. Opening 24 is provided in the cylindrical side surface of the central housing section 14 to permit the flexible tube 22 to pass loosely out of the handpiece near its point of connection to the inner tubular member 48.

Anterior section 12 of the handpiece housing receives and supports, by a press fit or other suitable means, the proximal portion of the outer tubular member 18 in which the inner tubular member 48 is slidably received. Anterior housing section 12 includes an internally threaded portion 50 for engaging a corresponding externally threaded portion 52 on the forward end of the central housing section 14. Prior to assembling these two sections, coupling member 42 is inserted into the forward end of the central housing section 14 so that the open cavity 43 of the coupling member faces the opening 24. The end of flexible tube 22 is then threaded through the opening 24 and cavity 43 so that it projects through the forward end 52 of the central housing section 14. The end of the flexible tube 22 may then be connected to the proximal end 46 of the inner tubular member 48 and secured by a suitable adhesive if desired. Coil spring 54 is now placed around inner tubular member 48 so as to encircle the same along the portion just forward of the platform member 44. At this point the inner tubular member 48 is inserted into the anterior housing portion 12 and thence into sliding coaxial relationship with the interior of the outer tubular member 18. Anterior housing section 12 may now be threaded onto the forward end 52 of the central housing section 14, which causes the return spring 54 to be compressed between the platform member 44 and the forward interior surface 56 of the anterior housing section 12. Preferably, the forward cylindrical cavity 62 that receives the coil spring 54 in the anterior housing section 12 is made not much larger in diameter than the spring itself in order to facilitate alignment of the spring during assembly of the handpiece and to insure that the spring is compressed uniformly, without bends or kinks, during the operation of the handpiece.

The manner in which the handpiece operates will now be readily apparent. The compressed condition of coil spring 54 between platform member 44 and the forward interior surface 56 of the anterior housing section 12 maintains coupling member 42 in firmly abutting relationship with the pusher member 32 at one end of the coupling member and with the platform member 44 at the opposite end of the coupling member. Application of positive pneumatic pressure pulses to the pneumatic actuator 30 causes forward linear displacement of the pusher member 32 toward the anterior end of the handpiece. Coupling member 42, which includes a conical depression 58 on one end thereof for firmly abutting the conical end of the pusher member 32, transmits the forward displacement of the pusher member 32 to the platform member 44. Platform member 44 is thus displaced to the forward limit of its travel, defined by the annular shoulder 60, thereby sliding inner tubular member 48 forward by an equal distance within the fixed outer tubular member 18. As a result of this forward displacement, coil spring 54 is further compressed between the platform member 44 and the forward interior surface 56 of the anterior housing section. When the pressure pulse terminates, pusher member 32 is restored to its rest position by the internal spring return of the actuator 30, and compressed coil spring 56 restores platform member 44, coupling member 42 and inner tubular member 48 to their normal retracted positions (clearly, the internal spring return of the pneumatic actuator 30 can be omitted if the coil spring 54 is sufficiently strong to restore the pusher member 32 as against any internal friction in the actuator 30). This cycle is repeated rapidly, typically several times each second, during normal use of the handpiece to carry out an endophthalmic surgical procedure.

It is important to note that, by virtue of the coupling member 42, the point of connection of the flexible suction or infusion tube 22 to the proximal end 46 of the inner tubular member 48 is completely isolated from the pneumatic pressure pulses supplied to the pneumatic actuator 30 without the need for the elaborate sealing arrangements employed in prior art handpieces. Moreover, the loose fit between the hole 24 and the flexible tube 22 effectively vents the coupling member receiving cavity 41 to the atmosphere, precluding any possibility of pneumatic continuity between the actuator 30 and the interior of the eye through either of the coaxial tubular members 18 and 48. In addition, by directing the flexible tube 22 out the side of the handpiece at a point adjacent the coupling member, concentric passageways are avoided and a simple tandem or in-line arrangement of the various components is preserved, allowing the handpiece to be of minimum overall dimensions. In the applicants' prototype, for example, the maximum outside diameter of the assembled handpiece measures only about three-eighths of an inch.

The preferred configuration of the coupling member 42 is shown in detail in FIG. 4. In general, the coupling member comprises a substantially semicylindrical portion 64 having a substantially semicylindrical open cavity 43 therein, and an enlarged closed end portion 66 for abutting the pusher member 32 of the pneumatic actuator 30. The open cavity 43 extends to and opens onto the end of the coupling member which abuts the platform member 44 in the assembled handpiece (shown in FIG. 3) in order to provide clearance for the attachment of the flexible suction or infusion tube 22 to the proximal end 46 of the inner tubular member 48. As FIG. 3 further illustrates, the dimensions of the open cavity 43 are sufficient to receive a lengthwise portion of the flexible tube 22. This allows sufficient room for the tube 22 to bend smoothly away from the proximal end 46 of the inner tubular member, where the tube 22 is aligned with the longitudinal axis of the inner tubular member 48, to the opening 24 in the cylindrical side surface of the central housing section 14, where the path of the tube 24 forms an angle with respect to the longitudinal axis of the inner tubular member 48.

To promote the aforesaid smooth bending of the flexible tube 22, the closed end portion 66 of the coupling member 42 is provided with an inclined guide surface 68 adjacent the open semicylindrical cavity 43. In addition, the rear wall portion 70 of the opening 24 has an inclination similar to that of the inclined surface 68 (preferably, the entire wall surface of the opening 24 is thus inclined, as shown in FIG. 3). In this way, as the coupling member 42 is reciprocated back and forth during the operation of the handpiece, at least one of the inclined surfaces 68 and 70 is acting as a guide surface for the flexible tube 22 at any given time. In practice, however, given the relatively small distance traversed by the coupling member 42 during its reciprocation (typically on the order of 0.4 mm.), the inclined surfaces 68 and 70 are never appreciably out of alignment. In effect, therefore, the inclined surfaces 68 and 70 continuously cooperate to cause the flexible tube 22 to bend smoothly as shown. It should be noted that, although FIG. 3 shows the flexible tube 22 to be separated from the inclined surfaces 68 and 70 for purposes of clarity, in reality the inherent resiliency of the tube 22 will tend to urge it into contact with these surfaces as it passes through the opening 24. The opening 24 is made substantially larger than the outside diameter of the flexible tube 22, as shown, in order to provide a loose fit between the opening and the flexible tube as noted previously.

Given the relatively small distance traversed by the reciprocating parts of the handpiece, there is no requirement of extraordinary flexibility for the suction or infusion tube 22. Standard one-sixteenth inch diameter tubing, as used in the applicants' prototype, possesses more than adequate flexibility for this purpose. If desired, the flexible tube 22 may be fastened to the rear of the handpiece 10 or to the pneumatic supply line 20 (shown in FIG. 1) to streamline the appearance of the handpiece, but some slack should be preserved in the tube 22 at its point of emergence from the opening 24 to avoid crimping the tube or interfering with the reciprocation of the inner tubular member 48.

The manner in which the handpiece of the present invention allows convenient interchangeability of endophthalmic surgical instruments may now be described with reference to FIG. 3. The projecting tubular surgical instrument shown in FIG. 3, which may assume various specialized forms depending on the endophthalmic procedure to be carried out, consists generally of an outer tubular member 18 whose proximal end is affixed to the anterior housing sectin 12, and a coaxial inner tubular member 48 slidably received within the outer tubular member 18 for reciprocation therein. To remove the instrument, it is necessary merely to uncouple the anterior housing section 12 from the posterior housing section comprising coupled housing sections 14 and 16, and to disconnect the flexible tube 22 from the proximal end 46 of the inner tubular member 48. Since there is no rigid mechanical connection between the coupling member 42 and the platform member 44, other than a physically abutting relationship, these two components separate readily. When removed, the anterior housing section 12 carries with it, besides the endophthalmic instrument itself, only the attached platform member 44 and the return spring 54. Functionally, these components together constitute a relatively minor portion of the assembled handpiece, given that the pneumatic actuating components remain behind as part of the main body of the handpiece. This renders it convenient and economical to provide a number of different surgical instruments for use with the same handpiece.

Reassembly of the handpiece with a new endophthalmic instrument and anterior housing portion is accomplished by threading the flexible tube 22 through the opening 24 and coupling member cavity 43, connecting the tube 22 to the proximal end of the new inner tubular member 48, and coupling the new anterior housing section 12 to the main body of the handpiece. To further facilitate this operation, the threaded coupling between the anterior section 12 and the central housing section 14 may be replaced by a locking cam-type coupling or other quickly engageable coupling arrangement. If desired, coupling member 42 may be adhesively bonded to the pusher member 32 of the pneumatic actuator 30 to prevent the coupling member from slipping out of the handpiece during the substitution of a new surgical instrument.

Reassembly of the handpiece may also be facilitated by extending the opening 24 to the forward edge of the central housing section 14 to form an open-ended slot. It is then merely necessary to align the flexible tube 22 with the slot and with the coupling member cavity 43 prior to attaching the new anterior housing section 12, without having to thread the tube 22 through a confined opening. When the anterior housing section 12 has been attached, however, its rear edge closes off the open end of the slot to form a functional equivalent of the opening 24.

The housing sections, coupling member and platform member of the handpiece may be molded or machined from any suitable material. Stainless steel is an appropriate material if it is intended to sterilize the handpiece in an autoclave. If gas sterilization will be employed, Delrin or other suitable thermoplastics may be used. Regardless of the material chosen, it will be apparent that the structural arrangement of the present handpiece does not require close dimensional tolerances for these components and therefore allows the handpiece to be easily and inexpensively manufactured.

FIGS. 5A and 5B are enlarged side sectional and plan views, respectively, of the distal portion of an endophthalmic vitrectomy instrument which may be accommodated by the handpiece of the present invention. Outer tubular member 18, which may be made from 20-gauge stainless steel hypodermic tubing, is press-fitted at its proximal end into the anterior housing section 12 of the handpiece as explained previously. At its distal end, the outer tubular member is closed off by welding and provided with an aperture 72 having a sharpened internal edge 74. Inner coaxial tubular member 48, which is slidably received within the outer tubular member 18 for reciprocation therein, is open at its distal end and sharpened at the lower edge 76 thereof. The proximal end of the inner tubular member, indicated at 46 in FIG. 3, is connected to a source of suction through the flexible tube 22 for drawing vitreous tissue or other intraocular material to be severed into the aperture 72. As the sharpened edge 76 of the inner tubular member repeatedly reciprocates past the sharpened edge 74 of the aperture, the tissue drawn into the aperture 72 is severed and evacuated from the eye in small bits through the inner tubular member 48 by the suction source and collected in a suitable receptacle. Saline infusion to replace lost volume and maintain positive intraocular pressure is preferably provided from an elevated saline column through a separately inserted cannula; alternatively, saline infusion may be provided through the handpiece by means of an infusion conduit (not shown) concentric with the outer tubular member 18.

An automatic pneumatic clamping device may be provided for cooperation with the flexible tube 22 in order to cut off the suction supply and dissipate any residual negative pressure in the inner tubular member 48 at the end of each cycle of operation of the handpiece. The details of such a system are disclosed in the applicants' copending application Ser. No. 097,983, filed on even date herewith and entitled "Apparatus and Process for Aspirating and Evacuating a Surgical Instrument", which application is expressly incorporated herein by reference.

The sharply raked shape of the vitrectomy instrument of FIGS. 5A and 5B that results from the sloping distal ends of the outer and inner tubular members 18 and 48 has been found to facilitate penetration of the outer wall of the eye by the vitrectomy instrument, as compared with blunt-end instruments, while avoiding the need to locate the aperture 72 inconveniently far back from the distal end of the instrument as is the case in most presently available instruments having symmetrically rounded or pointed distal ends to facilitate penetration of the eye. Due to the asymmetrical distal end configurations of the inner and outer tubular members of FIGS. 5A and 5B, however, they must be maintained in a fixed rotational relationship as viewed along their longitudinal axes. Referring to FIGS. 2 and 3, this requirement may be satisfied by providing the platform member 44 with a projecting key 78 for engaging a corresponding longitudinal groove 80 formed on the interior surface of the anterior housing section 12 of the handpiece (equivalently, the key may be formed on the inside surface of the anterior housing section and the groove on the platform member). Since the key-and-groove arrangement is thus confined to the separable or interchangeable anterior part of the handpiece, it need only be provided for instruments requiring a fixed rotational orientation. Provision for fixed rotational orientation does not, therefore, have to be made as between the components in the main body of the handpiece.

FIGS. 6A and 6B are enlarged side sectional and plan views, respectively, of an alternative endophthalmic instrument which may be accommodated by the pneumatic handpiece of the present invention. As before, outer tubular member 118 may be 20-gauge stainless steel hypodermic tubing which is pressfitted at its proximal end into an anterior housing section 12. In this case, however, slidably received inner coaxial tubular member 148 terminates well short of the distal end of the outer tubular member and carries a flexible metallic wire 82. The distal end of the wire 82 is curved and sharpened at its extremity 84, where it projects through an aperture 86 formed at the extreme distal end of the outer tubular member 118. Reciprocation of the inner tubular member 148 urges the forward part of the flexible wire 82 against the curved distal inside surface of the outer tubular member 118, which in turn causes the sharpened extremity 84 of the wire to project farther out of the aperture 86. This instrument may be used, for example, to define a line of perforations in the lens capsule of the eye in a lensectomy procedure. Although tissue evacuation is not necessary when this instrument is used, the open-ended inner tubular member 148 may be used to conduct a saline infusion into the eye by means of the flexible tube 22 to replace lost intraocular fluids and maintain positive intraocular pressure. A key-and-groove arrangement similar to that described previously may be provided between the platform member and the anterior housing section in which the instrument is received, but precise rotational alignment of the inner and outer tubular members is not critical in this instrument and the key-and-groove arrangement may therefore be omitted.

It is to be understood that the configuration of the projecting tubular surgical instrument of the present handpiece is not limited to either of the two particular types described above, and may assume a variety of different specialized configurations depending upon the particular endophthalmic procedure in which the instrument is to be used. Examples of known instrument configurations may be found, for example, in U.S. Pat. Nos. 3,776,238, to Peyman et al., 3,994,297, to Kopf, 4,011,869, to Seiler, Jr., and in 3,815,604, 3,884,237 and 3,884,238, all to O'Malley et al.

Although the present invention has been described with reference to a preferred embodiment, many modifications may be made thereto without departing from the spirit and scope of the invention. For example, while the coupling member is preferably left free-floating between the platform member and the pneumatic actuator as described, it may instead be adhesively bonded to the pusher member of the pneumatic actuator, if desired, without affecting the interchangeability feature of the handpiece. If interchangeability of surgical instruments is not required, the coupling member may also be bonded to the platform member. All such modifications are intended to be embraced within the scope of the appended claims.

What is claimed is:

1. A powered handpiece for endophthalmic surgery comprising:
  (a) a projecting tubular surgical instrument including coaxial inner and outer tubular members, said inner tubular member being slidably received within said outer tubular member for linear reciprocation therein;
  (b) a platform member rigidly attached to said inner tubular member near the proximal end thereof such that the proximal end of said inner tubular member extends beyond said platform member by a distance sufficient to permit the connection of a flexible tube to the proximal end of said inner tubular member;
  (c) a pneumatic linear actuator for producing linear reciprocating motion from a pneumatic power source;
  (d) a coupling member interposed between said pneumatic linear actuator and said platform member for transmitting linear reciprocating motion from said pneumatic actuator to the inner tubular member of said projecting tubular surgical instrument, one end of said coupling member being contoured for abutting said platform member in order to transmit linear reciprocating motion thereto while providing clearance for the connection of a flexible tube to the proximal end of said inner tubular member which extends beyond the platform member for carrying out suction or infusion through said inner tubular member during linear reciprocation thereof, said coupling member being maintained in simple abutting contact with the platform member without rigid mechanical connection thereto;
  (e) a return spring operatively associated with the inner tubular member of said projecting tubular surgical instrument for acting in opposition to the motion produced by said pneumatic linear actuator as transmitted to said inner tubular member by said coupling member; and
  (f) a housing for receiving said return spring, said coupling member, said pneumatic linear actuator, said platform member, and the proximal portion of said projecting tubular surgical instrument, said housing comprising:
    (1) an anterior section for receiving the return spring, the platform member and the proximal portion of said projecting tubular surgical instrument;
    (2) a posterior section for receiving in tandem arrangement said pneumatic linear actuator and said coupling member; and
    (3) means for releasably coupling the anterior and posterior sections of said housing so as to bring said one end of the coupling member into abutting contact with the platform member.

2. A powered handpiece for endophthalmic surgery as claimed in claim 1, wherein said return spring comprises a coil spring encircling said inner tubular member along a portion thereof and compressed between said platform member and an interior surface of the anterior section of said housing.

3. A powered handpiece for endophthalmic surgery as claimed in claim 2, wherein said platform member is generally cylindrical and coaxial with said inner tubular member, and wherein said coupling member comprises:
   (a) a substantially semicylindrical portion having a substantially semicylindrical open cavity therein, said cavity extending to and opening onto the end of said coupling member which abuts the platform member to provide said clearance, said cavity further having dimensions sufficient to receive a lengthwise portion of a flexible tube which has been connected to the proximal end of said inner tubular member; and
   (b) a closed end portion opposite the end of said coupling member which abuts the platform member and adjoining said substantially semicylindrical portion for abutting said linear actuator in order to receive linear reciprocating motion therefrom, said closed end portion including an inclined guide surface adjacent said substantially semicylindrical cavity for causing a flexible tube which has been connected to the proximal end of said inner tubular member, and a lengthwise portion of which is received in said substantially semicylindrical cavity, to bend smoothly to form an angle with respect to the line defined by the longitudinal axis of the inner tubular member, and further wherein the confirgurations of said anterior and posterior housing sections are generally cylindrical, said posterior housing section having an opening in the cylindrical side surface thereof at a point adjacent said coupling member for allowing said flexible tube to pass loosely out of said posterior housing section at said angle.

4. A powered handpiece for endophthalmic surgery as claimed in claim 3, wherein at least a portion of the wall of said opening is inclined similarly to said inclined guide surface, whereby said inclined guide surface and the similarly inclined wall portion of said opening cooperate to cause the flexible tube to bend smoothly at said angle.

5. A powered handpiece for endophthalmic surgery as claimed in claim 4, wherein the outer tubular member of said projecting tubular surgical instrument has an aperture therein near the distal end thereof for receiving intraocular material to be severed, and wherein the inner tubular member of said projecting tubular surgical instrument has a sharpened edge at the distal end thereof for severing the intraocular material received in said aperture as said sharpened edge reciprocates past said aperture, and further wherein the platform member includes a projecting key for engaging a longitudinal groove formed on an interior surface of the anterior section of the housing, whereby a fixed rotational relationship is maintained between said inner tubular member and said outer tubular member.

* * * * *